US012797607B2

(12) United States Patent
Bowe et al.

(10) Patent No.: US 12,797,607 B2
(45) **Date of Patent: *Nov. 17, 2026**

(54) LEAD ENGAGEMENT DEVICE

(71) Applicant: KONINKLIJKE PHILIPS N.V., Eindhoven (NL)

(72) Inventors: Wade Allen Bowe, Colorado Springs, CO (US); Jeff Payne, Murrieta, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 632 days.

This patent is subject to a terminal disclaimer.

(21) Appl. No.: 17/602,769

(22) PCT Filed: Apr. 16, 2020

(86) PCT No.: PCT/EP2020/060677
§ 371 (c)(1),
(2) Date: Oct. 10, 2021

(87) PCT Pub. No.: WO2020/221593
PCT Pub. Date: Nov. 5, 2020

(65) Prior Publication Data

US 2022/0152383 A1 May 19, 2022

Related U.S. Application Data

(60) Provisional application No. 62/840,742, filed on Apr. 30, 2019.

(51) Int. Cl.
*A61N 1/05* (2006.01)

(52) U.S. Cl.
CPC ...... *A61N 1/057* (2013.01); *A61N 2001/0578* (2013.01)

(58) Field of Classification Search
CPC .. A61N 1/0558; A61N 1/37518; A61N 1/057; A61N 2001/0578; A61B 2017/22034
See application file for complete search history.

(56) References Cited

U.S. PATENT DOCUMENTS

2004/0236396 A1* 11/2004 Coe ........................ A61N 1/057
607/116
2005/0070986 A1 3/2005 Tockman et al.
(Continued)

FOREIGN PATENT DOCUMENTS

WO 2006089039 A2 8/2006

OTHER PUBLICATIONS

International Search Report and Written Opinion of PCT/EP2020/060677, dated Jun. 26, 2020.
(Continued)

*Primary Examiner* — Ankit D Tejani

(57) ABSTRACT

A lead engagement device is configured to be positioned in a lead lumen of a lead. The lead engagement device includes a hypotube, and the hypotube includes a wall having an inner surface defining an inner lumen and an outer surface opposite the inner surface. A plurality of lead engagement fingers are coupled to the wall and extend outwardly and proximally from the outer surface. Each of the fingers is disposed adjacent to one of a plurality of apertures that extend through the wall. The fingers are configured to permit relative motion between the lead engagement device and the lead when applying a first force to the lead engagement device. The fingers are also configured to engage the lead and inhibit relative motion between the lead engagement device and the lead when applying an opposite second force to the lead engagement device.

15 Claims, 11 Drawing Sheets

(56) References Cited

U.S. PATENT DOCUMENTS

| | | | | |
|---|---|---|---|---|
| 2012/0053665 | A1* | 3/2012 | Stolz | A61N 1/0558 607/118 |
| 2018/0028779 | A1 | 2/2018 | Von Oepen | |
| 2019/0030324 | A1 | 1/2019 | Grace | |

OTHER PUBLICATIONS

Kennergren, Charles et al., "Cardiac Lead Extraction with a Novel Locking Stylet", Journal of Interventional Cardiac Electrophysiology, vol. 4, pp. 591-593 (2000). Abstract Only.

* cited by examiner

LEAD ENGAGEMENT DEVICE

CROSS-REFERENCE TO RELATED APPLICATION

The present application claims the benefit of U.S. Provisional Application Ser. No. 62/840,742, filed Apr. 30, 2019 which is hereby incorporated by reference herein.

FIELD OF THE DISCLOSURE

The devices described herein generally relate to lead engagement devices for engaging and facilitating removal of an implanted lead, such as a cardiac implantable electronic device ("CIED") lead, from a patient's body, and more specifically relate to lead engagement devices providing relatively large areas for engaging implanted leads.

BACKGROUND

Various medical procedures attach wire-like devices to internal portions of a patient's body, such as an electrical lead for a cardiac implantable electronic device ("CIED"). CIED leads are electrically conductive wires which run to an electrode that is attached to an inner wall of a patient's heart. CIED leads are typically a coil of wire enclosed in an outer cylindrical sheath of electrically insulating material. The coil of wire usually leaves a hollow space running down the center of the CIED lead (a "lumen").

CIED leads are usually implanted with the intention that they will remain in the patient for several years. During such time, fibrous tissue grows over the electrode and portions of the lead. CIED leads are often provided with additional barb-like structures or a corkscrew type of structure to encourage adhesion to the inner wall of the patient's heart.

CIED leads sometimes need to be removed for a variety of reasons including infection, malfunction, venous occlusion, advisory, etc.

Numerous lead engagement devices have thus been developed that can be inserted into the lumen of a CIED lead and attached to the CIED lead in order to apply traction to the lead. However, these devices typically have a disadvantage that they attach to the CIED lead in a localized area. Applying traction to the CIED lead and/or CIED lead engagement devices can result in the CIED lead becoming distorted and/or breaking before it can be removed from the patient.

Accordingly, it is desirable to provide improved lead engagement devices.

SUMMARY

The present disclosure presents a lead engagement device configured to be positioned in a lead lumen of a lead. The lead engagement device includes a hypotube, and the hypotube includes a wall having an inner surface defining an inner lumen and an outer surface opposite the inner surface. A plurality of apertures extend through the wall from the inner surface to the outer surface. A plurality of lead engagement fingers are coupled to the wall and extend outwardly and proximally from the outer surface. Each of the plurality of lead engagement fingers is disposed adjacent to one of the plurality of apertures. The plurality of lead engagement fingers are configured to permit relative motion between the lead engagement device and the lead when applying a first force to the lead engagement device. The plurality of lead engagement fingers are also configured to engage the lead and inhibit relative motion between the lead engagement device and the lead when applying a second force to the lead engagement device, the second force being applied in an opposite direction than the first force.

The lead engagement device according to the previous paragraph, wherein the inner lumen defines a longitudinal axis of the hypotube, the plurality of apertures are disposed in planes substantially parallel to the longitudinal axis of the hypotube, and the plurality of lead engagement fingers are normally disposed at acute angles relative to the longitudinal axis.

The lead engagement device according to any of the previous paragraphs, wherein a plane in which at least one of the acute angles is disposed substantially bisects the wall of the hypotube.

The lead engagement device according to any of the previous paragraphs, wherein at least one of the acute angles is normally in a range of 5 to 45 degrees.

The lead engagement device according to any of the previous paragraphs, wherein the inner lumen defines a longitudinal axis of the hypotube and circumferential direction extending about the longitudinal axis, wherein the plurality of fingers are curved in the circumferential direction.

The lead engagement device according to any of the previous paragraphs, wherein at least one of the plurality of lead engagement fingers has a distal end coupled to the wall, a proximal free end opposite the distal end, and length between the distal end and the proximal free end in a range of 0.01 to 0.25 inches.

The lead engagement device according to any of the previous paragraphs, wherein the plurality of lead engagement fingers are cantilevered from the wall.

The lead engagement device according to any of the previous paragraphs, wherein the plurality of lead engagement fingers monolithically couple to the wall.

The lead engagement device according to any of the previous paragraphs, wherein the plurality of lead engagement fingers have a first shape, the plurality of apertures have a second shape, the second shape being the same as the first shape.

The lead engagement device according to any of the previous paragraphs, wherein the first shape and the second shape are rectangles.

The lead engagement device according to any of the previous paragraphs, further comprising an outer sheath comprising an outer lumen, the outer lumen removably receiving the hypotube.

The present disclosure also presents a method for manufacturing a lead engagement device. The method includes providing a hypotube including a wall, the wall including an inner surface defining an inner lumen and an outer surface opposite the inner surface. The method further includes cutting the wall to form a plurality of lead engagement fingers. The method includes deforming the plurality of lead engagement fingers such that the plurality of lead engagement fingers normally extend outwardly and proximally from the outer surface.

The method according to the previous paragraph, wherein cutting the wall comprises laser cutting the wall.

The method according to any of the previous paragraphs, wherein deforming further comprises forming a plurality of apertures extending through the wall from the inner surface to the outer surface and disposed adjacent to the plurality of lead engagement fingers.

The method according to any of the previous paragraphs, wherein the inner lumen defines a longitudinal axis of the hypotube, and deforming the plurality of lead engagement fingers causes the plurality of lead engagement fingers to be normally disposed at acute angles relative to the longitudinal axis.

The method according to any of the previous paragraphs, wherein a plane in which at least one of the acute angles is disposed substantially bisects the wall of the hypotube.

The method according to any of the previous paragraphs, wherein at least one of the acute angles is in a range of 5 to 45 degrees.

The method according to any of the previous paragraphs, wherein cutting and deforming provides the plurality of lead engagement fingers with a distal end coupled to the wall, a proximal free end opposite the distal end, and length between the distal end and the proximal free end in a range of 0.01 to 0.25 inches.

The method according to any of the previous paragraphs, wherein cutting provides the plurality of lead engagement fingers with rectangular shapes.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
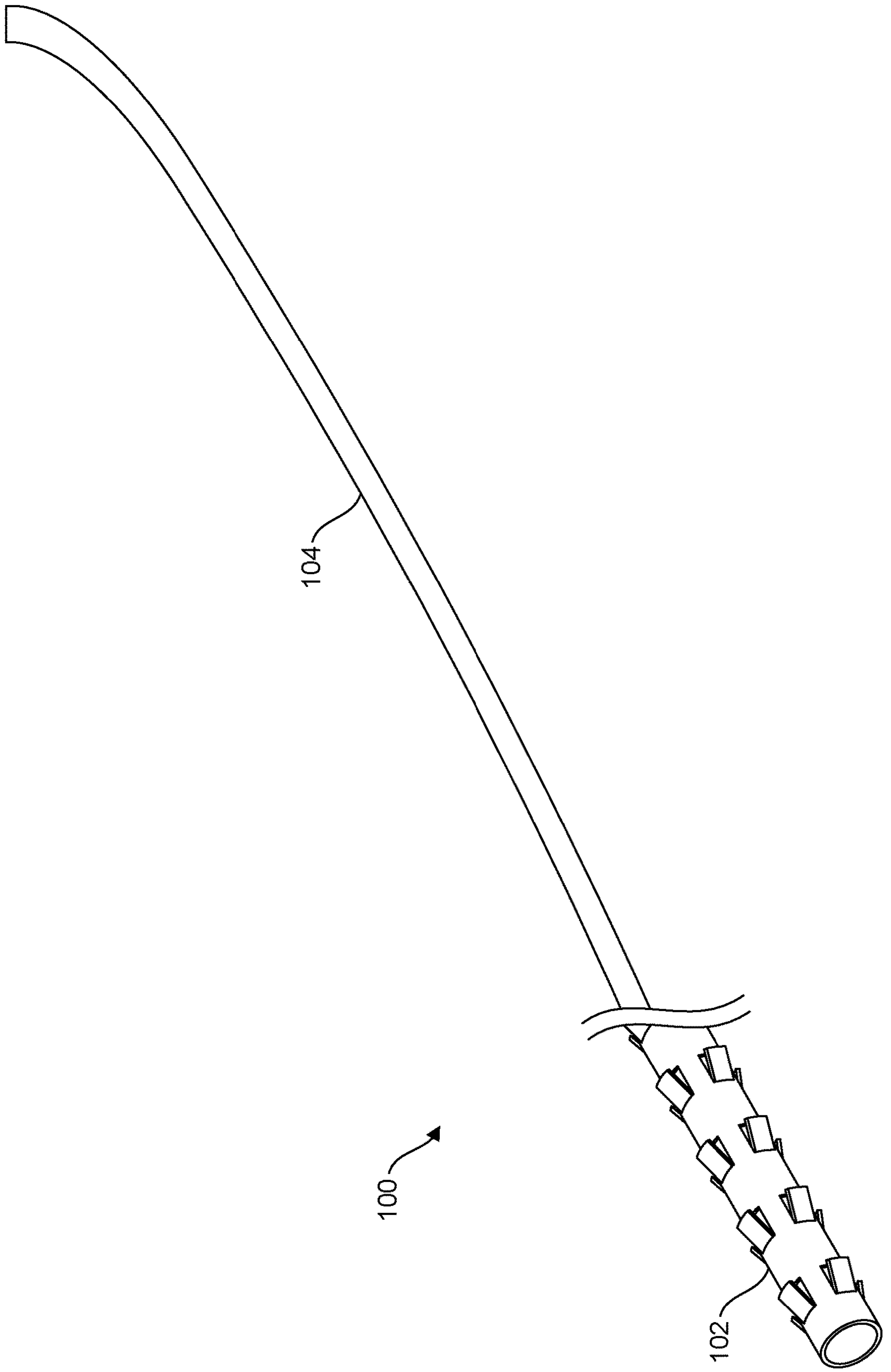
FIG. 1 is a perspective view of a lead engagement device according to an embodiment of the present disclosure.

The present disclosure relates generally to lead engagement devices for engaging and facilitating removal of an implanted lead, such as a cardiac implantable electronic device ("CIED") lead, from a patient's body. Referring to FIG. 1, there is shown an exemplary embodiment of the lead engagement devices described herein. The lead engagement device 100 generally includes a distal lead engagement portion 102 and a proximal handle portion 104. FIG. 1 omits a section of the lead engagement device 100, including an interface between the distal lead engagement portion 102 and the proximal handle portion 104, for illustrative purposes. Consequently, FIG. 1 does not illustrate the scaled length of the lead engagement device 100. The lead engagement device 100 may have a length of, for example, at least about 71 cm. However, the lead engagement device 100 may be provided with other lengths depending on the intended application.

With continued reference to FIG. 1, at least a portion of the proximal handle portion 104 remains external to a patient while the distal lead engagement portion 102 enters and engages an implanted lead during a lead removal procedure. As such, traction may be applied to the proximal handle portion 104 to remove the lead from the patient. The proximal handle portion 104 may be a wire, for example, a stainless steel wire, or a continuation of the hypotube without the apertures. The proximal handle portion 104 may include a loop (not shown) at a proximal end portion 106 to facilitate applying traction to the lead engagement device 100.

Referring now to FIGS. 2A-2D, the distal lead engagement portion 102 is illustrated. Generally, the distal lead engagement portion 102 is a hypotube 200 comprising one or more of various appropriate materials, such as stainless steel, nitinol, and the like. The hypotube 200 includes a wall 202 that defines an outer surface 204 and an opposite inner surface 206, and the inner surface 206 defines an inner lumen 208 of the hypotube 200. The outer surface 204 may have a diameter that facilitates positioning the distal lead engagement portion 102 within the lumen of lead. The diameter of the outer surface 204 may be, for example, about 0.013 to 0.027 inches. The diameter of the inner surface 206 may be, for example, about 0.010 to 0.024 inches. The inner lumen 208 defines a longitudinal axis 210 that extends from a distal opening 212 at a distal end portion 214 to a proximal opening (not shown) at a proximal end portion (not shown). The inner lumen 208 also defines a circumferential direction 216 that is perpendicular to and extends about the longitudinal axis 210. The wall 202 has a length between the distal opening 212 and the proximal opening of, for example, at least about 71 cm. In some embodiments, the hypotube 200 couples to a coil capped by a half sphere (not shown) near the distal opening 212.

The hypotube 200 further includes a plurality of apertures 218 and a plurality of adjacent lead engagement fingers 220. The apertures 218 and the lead engagement fingers 220 may both be formed, for example, by laser cutting and bending portions of the hypotube 200, as described in further detail below. Generally, the lead engagement fingers 220 extend outwardly from the outer surface 204 of the wall 202 proceeding away from the distal end portion 214 and toward the proximal end portion. Accordingly, the lead engagement fingers 220 engage a lead when the lead engagement portion 102 enters the lumen of the lead and permit unidirectional motion of the lead engagement portion 102 relative to the lead. More specifically, the lead engagement fingers 220 permit relative motion between the lead engagement portion 102 and the lead and slide relative to the lead when applying a first force to the lead engagement portion 102 (for example, applying a pushing force in a generally distal direction). The lead engagement fingers 220 also engage the lead and inhibit relative motion between the lead engagement portion 102 and the lead when applying a second force to the lead engagement portion 102, (for example, applying a pulling or traction force in a generally proximal direction).

Figure 2A:
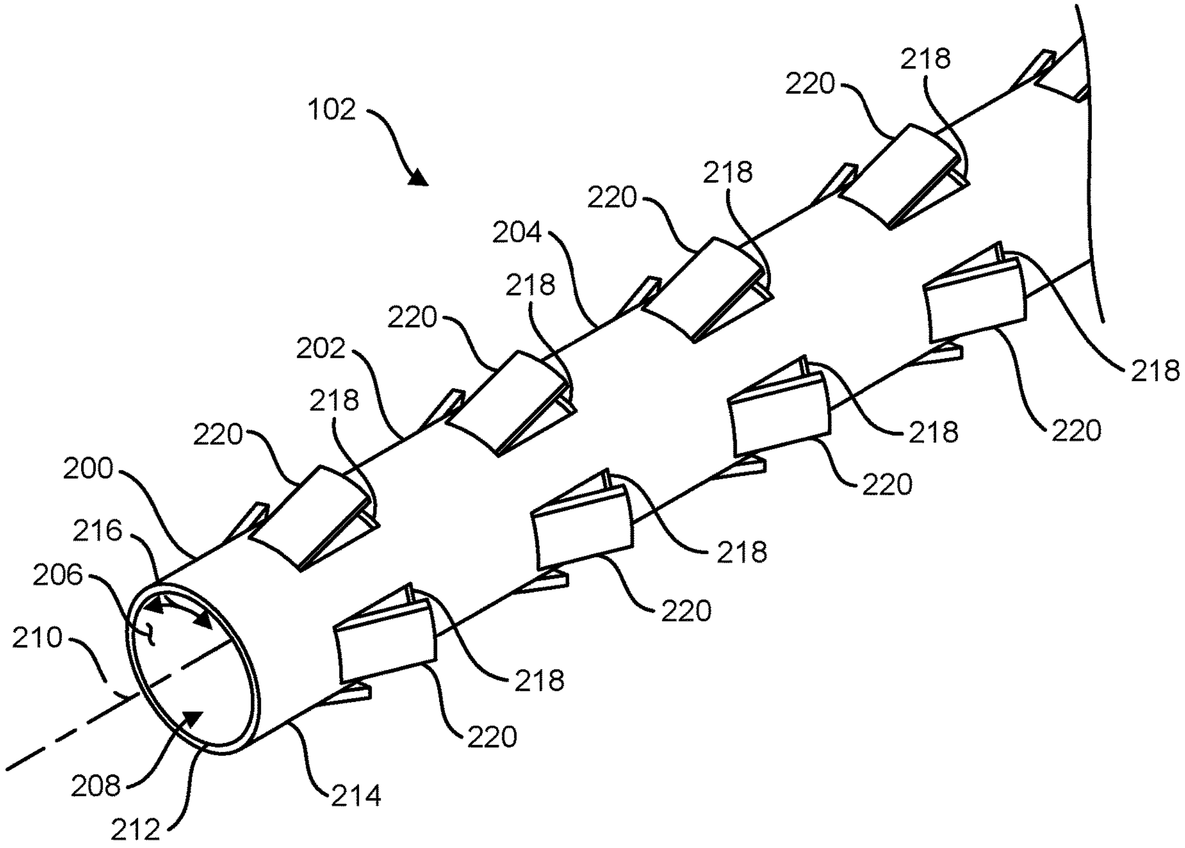
FIG. 2A is a detail perspective view of a distal lead engagement portion of the lead engagement device of FIG. 1.
Figure 2B:
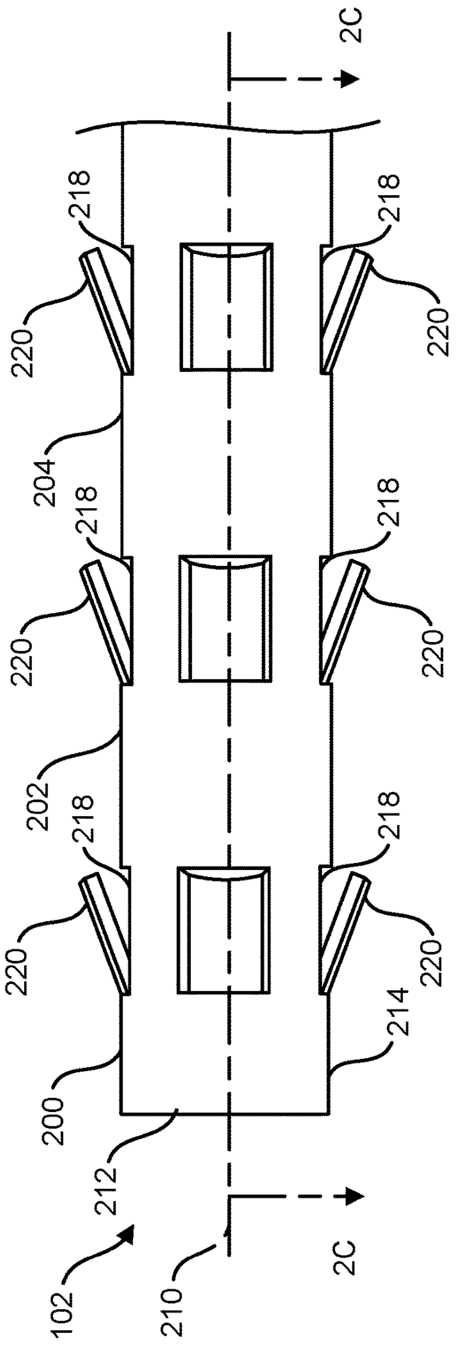
FIG. 2B is a side view of the lead engagement portion of FIG. 2A.
Figure 2C:
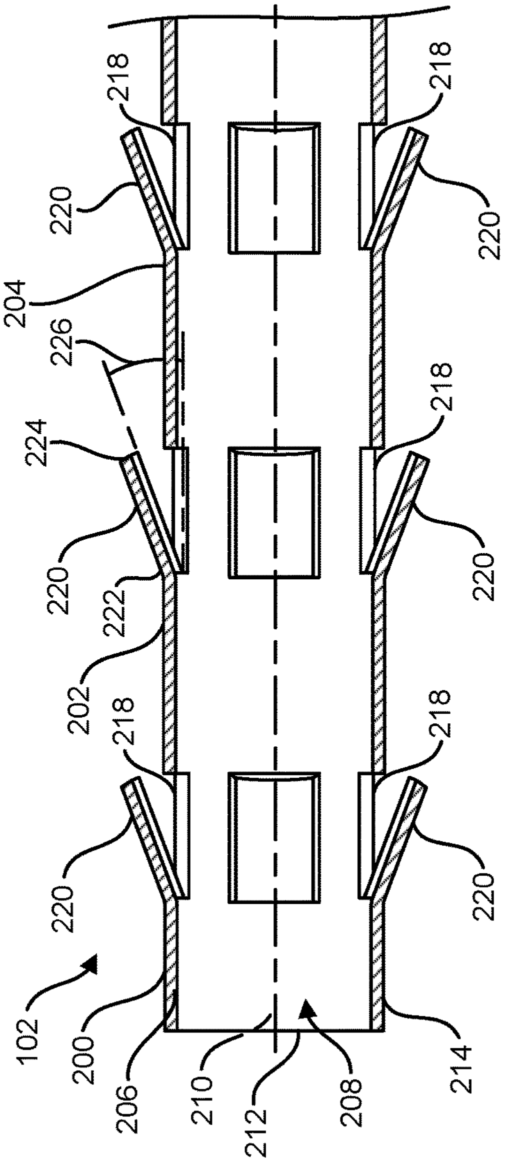
FIG. 2C is a transverse sectional view of the lead engagement portion along line 2C-2C of FIG. 2B.
Figure 2D:
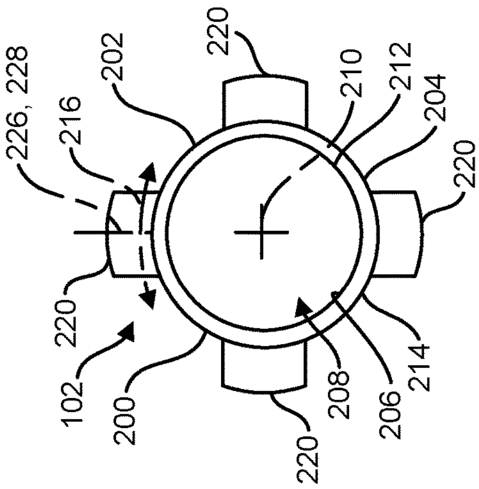
FIG. 2D is a distal end view of the lead engagement portion of FIG. 2A.

In some embodiments and as illustrated most clearly in FIG. 2C, each of the lead engagement fingers 220 has a distal end 222 coupled to the wall 202 and a proximal free end 224 opposite the distal end 222. In some embodiments and as illustrated, the lead engagement fingers 220 are monolithically coupled to and cantilevered from the wall 202 at their distal ends 222. Such a structure permits the lead engagement fingers 220 to (1) deflect radially inwardly and slide across the lead when the lead engagement portion 102 is advanced distally within the lumen of the lead, and (2) engage the lead and inhibit relative motion between the lead engagement portion 102 and the lead when applying traction to the lead engagement device 100.

The lead engagement fingers 220 and the apertures 218 may be provided in a variety of shapes, sizes, and arrangements. The apertures 218 extend through the wall 202 from the inner surface 206 to the outer surface 204. In some embodiments and as illustrated, the plurality of apertures 218 are disposed in planes that are substantially parallel to the longitudinal axis 210 of the hypotube 200. In some embodiments and as illustrated, the lead engagement fingers 220 are normally disposed at acute angles 226 relative to the outer surface 204 ("normally" and variants thereof referring to situations in which external forces are not applied to component). In some embodiments and as illustrated, planes 228 in which the acute angles 226 are disposed (see FIG. 2D) substantially bisect the wall 202 of the hypotube 200 (that is, bisect ±0.1 inches). In some embodiments and as illustrated, the acute angles 226 are normally in a range of 10 to 30 degrees.

In some embodiments, the lead engagement fingers 220 are generally present along the majority of the length of the hypotube 200. More specifically, the lead engagement fingers 220 may be present over a length in a range of 50 to 75 cm from a most-distal finger to a most-proximal finger. Accordingly, the lead engagement fingers 220 may provide a relatively large area for engaging implanted leads. In some embodiments, multiple lead engagement fingers 220 may be disposed at the same longitudinal position along the wall 202 of the hypotube 200 or grouped at various longitudinal positions. For example and as illustrated, four lead engagement fingers 220 may be disposed at each longitudinal position. Groups of lead engagement fingers 220 may be disposed apart by the same longitudinal distance, as illustrated, or different longitudinal distances. In some embodiments, each lead engagement finger may be disposed at a different longitudinal position than the other lead engagement fingers 220.

The fingers 220 may be provided in a variety of shapes. In some embodiments and as illustrated, each of the fingers 220 has a rectangular shape. The rectangular shape may have a length (between the distal end 222 and the proximal free end 224) of, for example, 0.010 to 0.250 inches. The rectangular shape may have a width (in the circumferential direction 216 of the wall 202) of, for example, 45 degrees. In other embodiments, one or more of the fingers 220 has a different shape, such as a triangular shape, a semi-elliptical shape, a semi-parabolic shape, or the like.

Each aperture 218 may have the same shape as the adjacent finger (although each aperture 218 may be slightly larger than the adjacent finger due to the manner in which the features are formed, as described in further detail below). In some embodiments and as illustrated, each of the apertures 218 has a rectangular shape. In other embodiments, one or more of the apertures 218 has a different shape, such as a triangular shape, a semi-elliptical shape, a semi-parabolic shape, or the like.

Figure 3A:
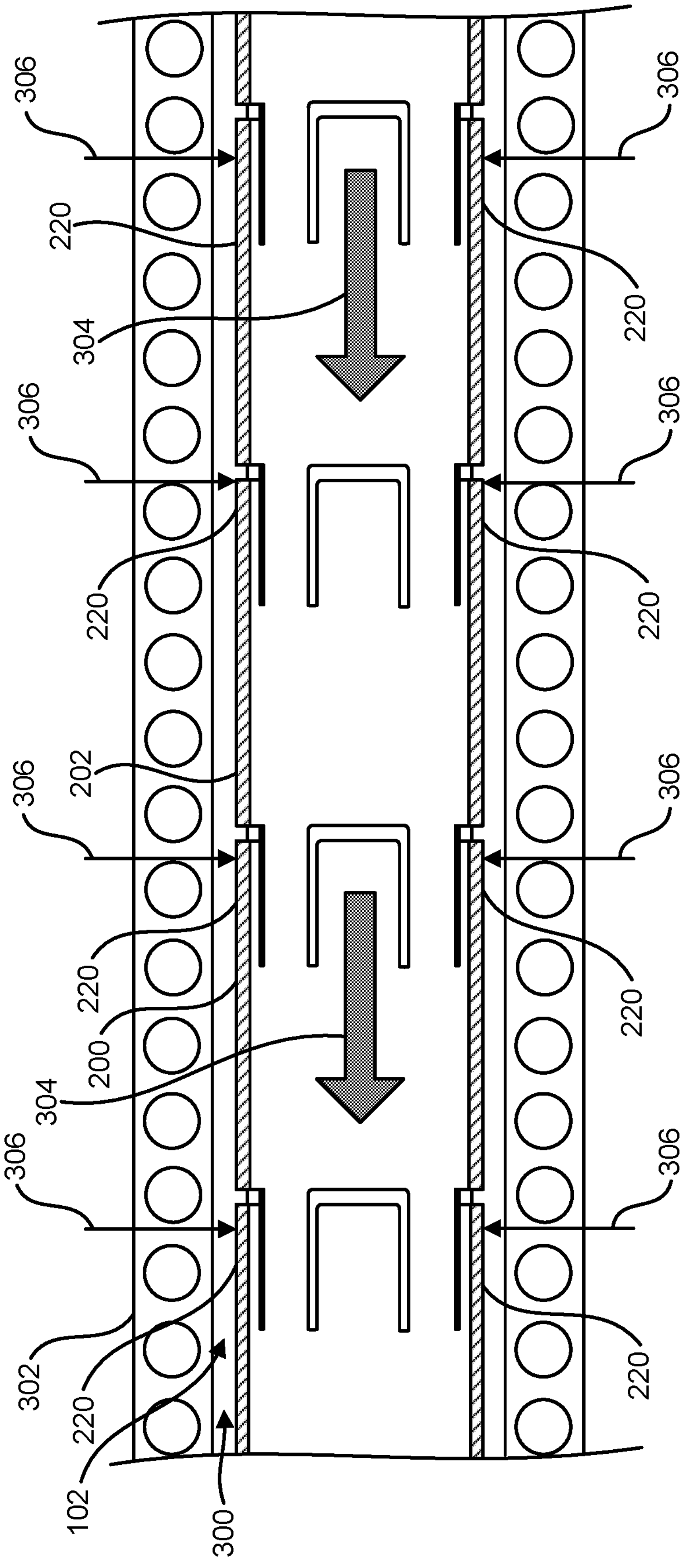
FIG. 3A is a transverse sectional view of the lead engagement portion of FIG. 2A disposed in a lumen of a lead.
Figure 3B:
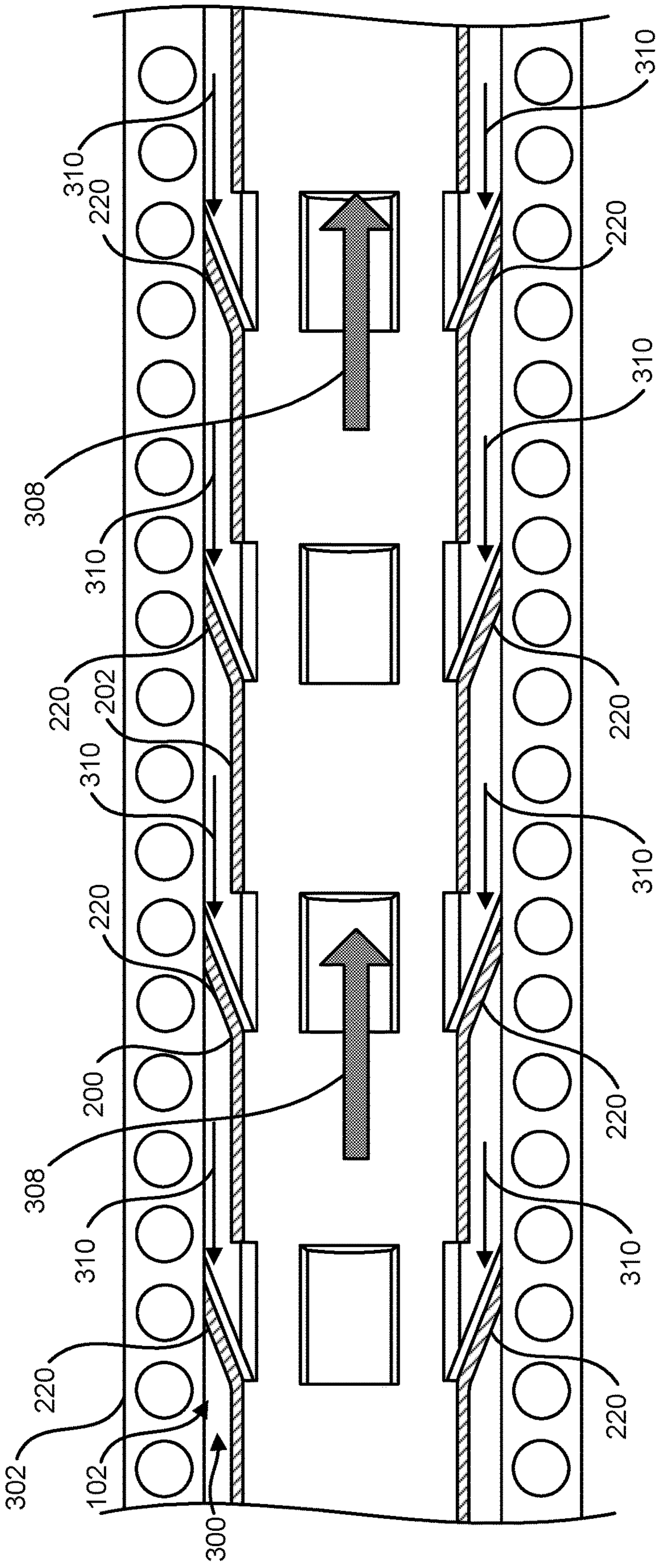
FIG. 3B is another transverse sectional view of the lead engagement portion of FIG. 2A disposed in the lumen of the lead.

FIGS. 3A and 3B illustrate the lead engagement portion 102 disposed in a lumen 300 of a lead 302. In FIG. 3A, a first or pushing force 304 is applied that urges the lead engagement portion 102 distally relative to the lead 302. In this situation, the lead 302 applies contact forces 306 to the lead engagement fingers 220, and the contact forces 306 cause the fingers 220 to deflect radially inwardly (the degree of deflection is exaggerated in FIG. 3A for illustrative purposes). Accordingly, the fingers 220 slide across the lead 302 and thereby permit the lead engagement portion 102 to move distally in the lumen 300 of the lead 302. In FIG. 3B, a second or pulling force 308 is applied that urges the lead engagement portion 102 proximally relative to the lead 302. However, in this situation the lead 302 applies resistance forces 310 to the fingers 220, and the resistance forces 310 cause the fingers 220 to deflect further radially outwardly. The fingers 220 thereby interfere with the lead 302 and inhibit the lead engagement portion 102 to move proximally in the lumen 300 of the lead 302. As such, the second force 308 acts as a traction force for removing the lead 302 from a patient.

Figure 4:
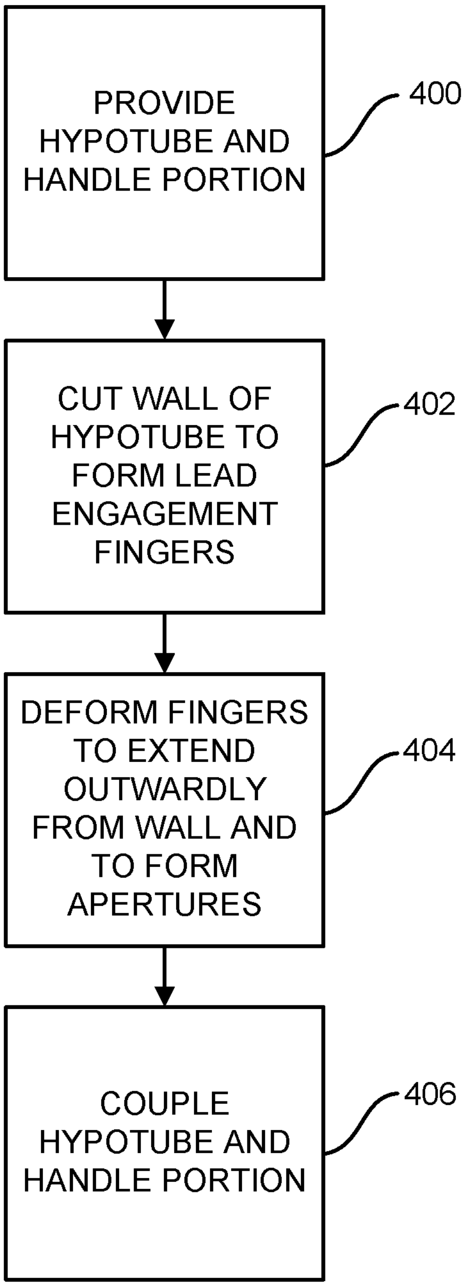
FIG. 4 is a diagram illustrating a method for manufacturing a lead engagement device according to an embodiment of the present disclosure.

FIG. 4 illustrates an exemplary method for manufacturing a lead engagement device according to the present disclosure. The description of the method refers to the lead engagement device 100 and components described above for illustrative purposes, and the method could be used for manufacturing any of the lead engagement devices according to the present disclosure. The method begins at block 400 by providing the hypotube 200 and the proximal handle portion 104. At block 402, the wall 202 of the hypotube 200 is cut (for example, laser cut) to form the plurality of lead engagement fingers 220. At block 404, the lead engagement fingers 220 are deformed (for example, mechanically bent) such that the fingers 220 normally extend outwardly and proximally from the outer surface 204 of the wall 202 of the hypotube 200 and to form the plurality of apertures 218. At block 406, the hypotube 200 and the proximal portion are coupled to each other (for example, via welding, crimping, or the like).

Figure 5A:
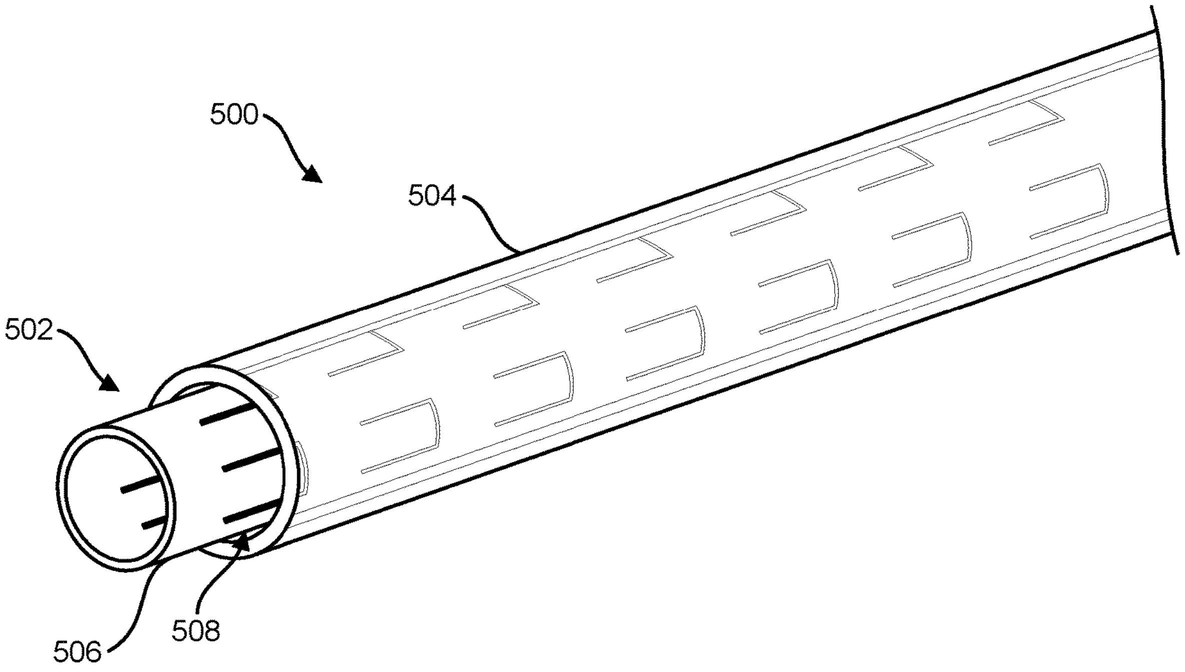
FIG. 5A is a perspective view of a lead engagement device according to another embodiment of the present disclosure in a stowed configuration.
Figure 5B:
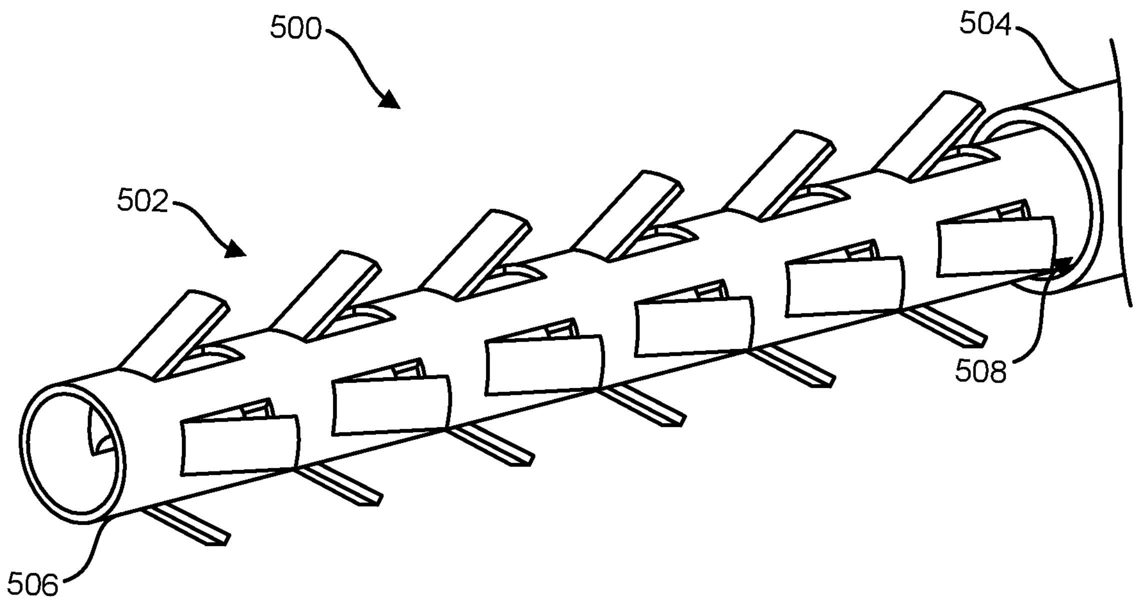
FIG. 5B is a perspective view of the lead engagement device of FIG. 5A in a deployed configuration.

Referring now to FIGS. 5A and 5B, another exemplary embodiment of a lead engagement device 500 according to the present disclosure is illustrated. The lead engagement device 500 generally includes a distal lead engagement portion 502 and a proximal handle portion (not shown), which may be the same or similar to the distal lead engagement portion 102 and a proximal handle portion 104 described above, respectively. The lead engagement device 500 further includes an outer sheath 504 that initially removably receives the hypotube 506 of the distal lead engagement portion 502. FIG. 5A illustrates the lead engagement portion 502 in an initial stowed configuration in which it is disposed within a lumen 508 of the outer sheath 504. FIG. 5B illustrates the lead engagement portion 502 in a deployed configuration in which it is exposed from the outer sheath 504.

Figure 6A:
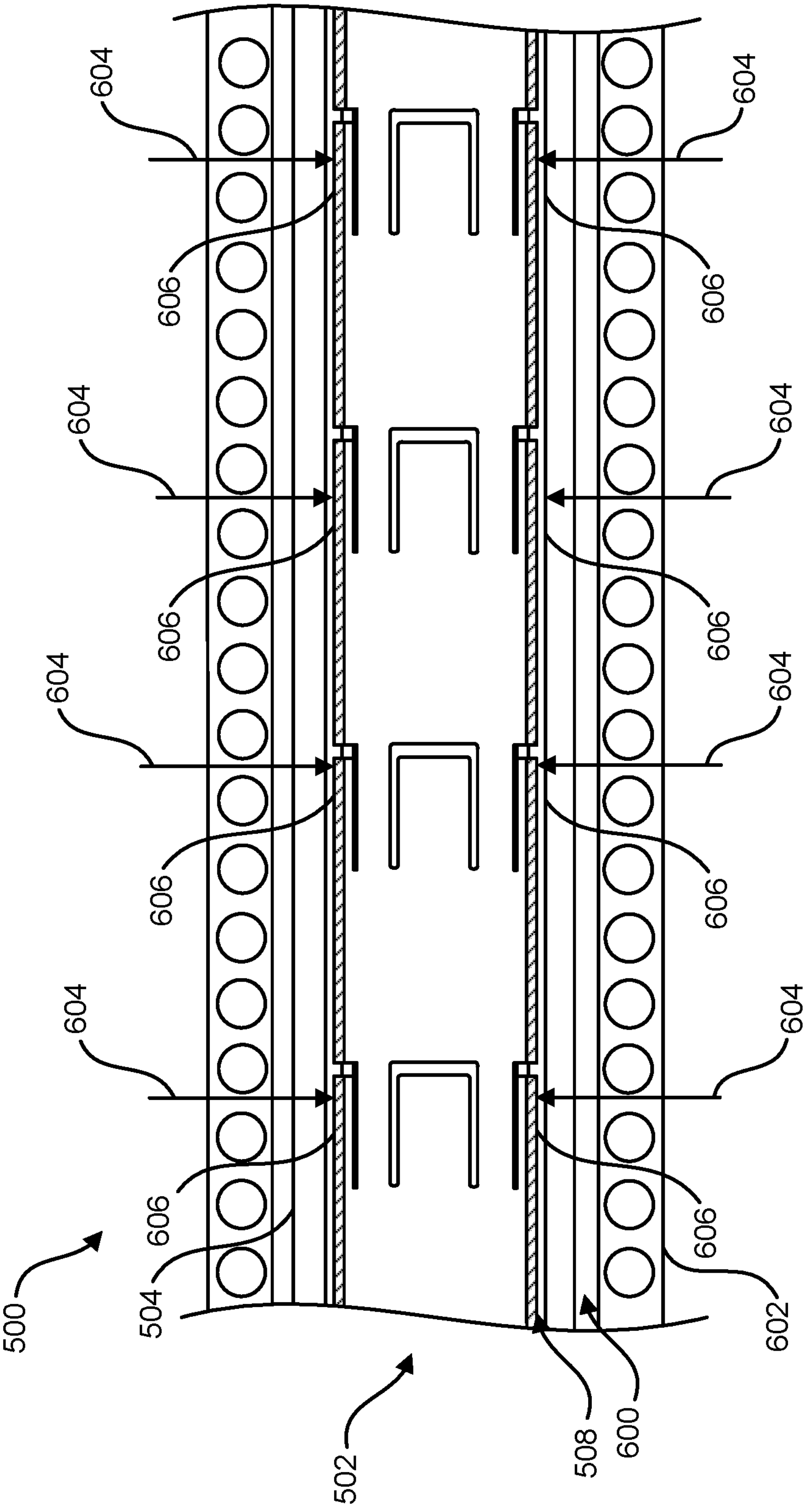
FIG. 6A is a transverse sectional view of a lead engagement portion of the lead engagement device of FIG. 5A disposed in a lumen of a lead and in the stowed configuration.
Figure 6B:
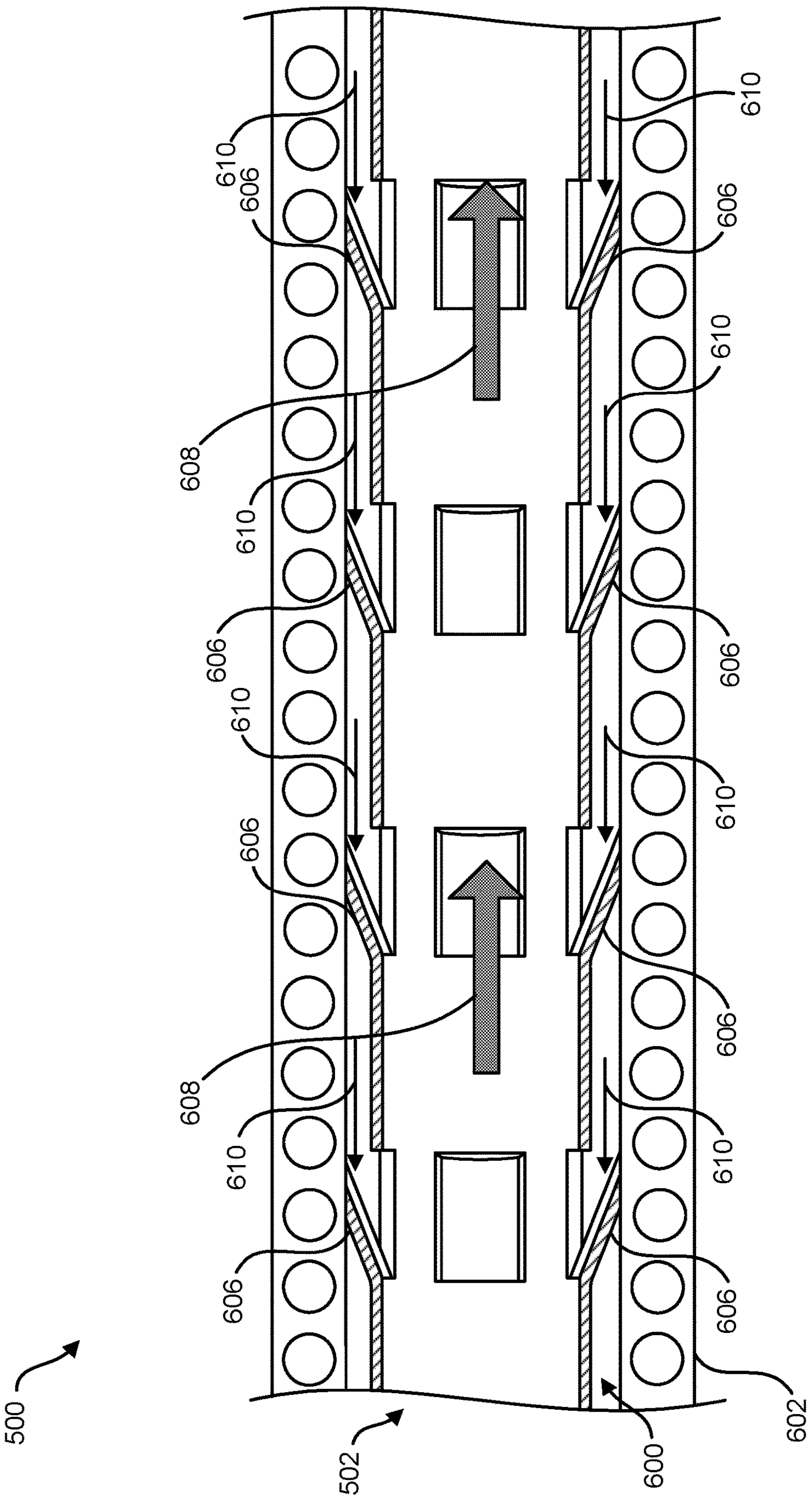
FIG. 6B is another transverse sectional view of a lead engagement portion of the lead engagement device of FIG. 5A disposed in the lumen of the lead and in the deployed configuration.

FIGS. 6A and 6B illustrate the lead engagement portion 502 disposed in a lumen 600 of a lead 602. In FIG. 6A, the distal lead engagement portion 502 is in the stowed configuration and received in the lumen 508 of the outer sheath 504. The outer sheath 504 applies contact forces 604 to the lead engagement fingers 606, and the contact forces 604 hold the fingers 606 radially inwardly. Accordingly, the lead engagement fingers 606 do not engage the lead 602 in the stowed configuration, and the distal lead engagement portion 502 and the outer sheath 504 may freely move within the lumen 600 of the lead 602 (both distally and proximally). In FIG. 6B, the distal lead engagement portion 502 is in the deployed configuration (for example, by pulling the outer sheath 504 proximally relative to the distal lead engagement portion 502). In the deployed configuration, a pulling force 608 may be applied that urges the lead engagement portion 502 proximally relative to the lead 602. However, in this situation the lead 602 applies resistance forces 610 to the fingers 606, and the resistance forces 610 cause the fingers 606 to deflect further radially outwardly. The fingers 606 thereby interfere with the lead 602 and inhibit the lead engagement portion 502 to move proximally in the lumen 600 of the lead 602. As such, the pulling force 608 acts as a traction force for removing the lead 602 from a patient.

Figure 7A:
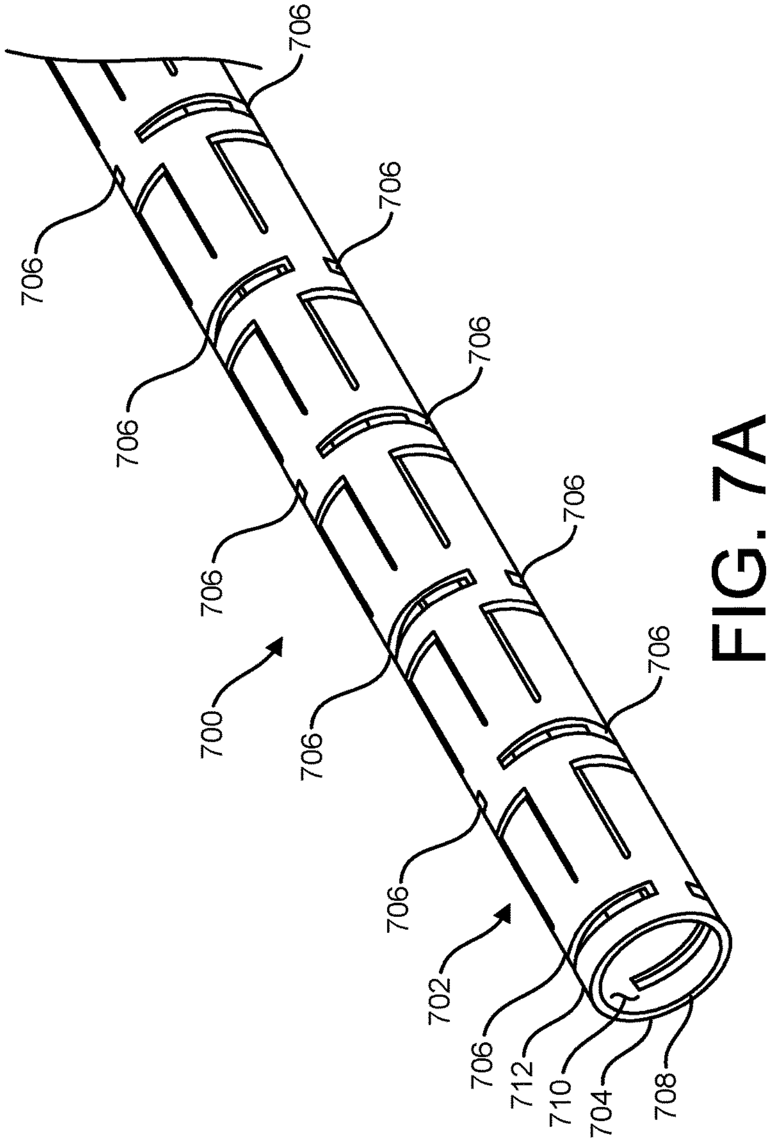
FIG. 7A is a perspective view of a lead engagement device according to another embodiment of the present disclosure.
Figure 7B:
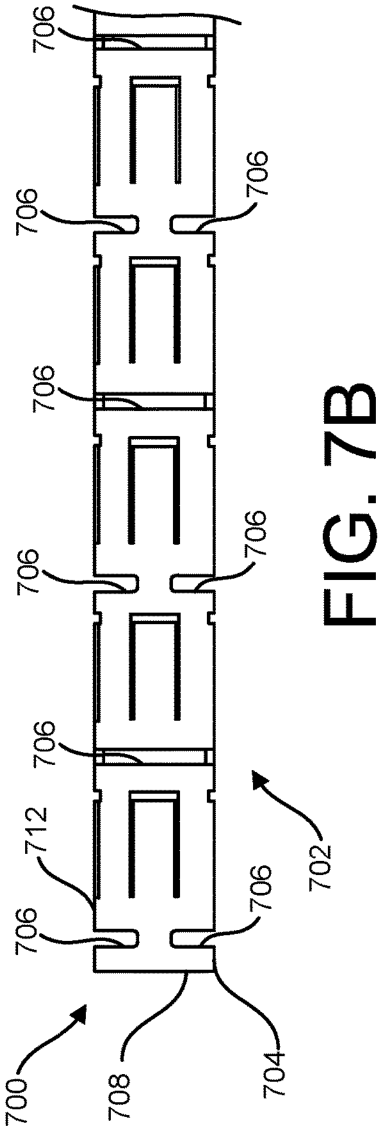
FIG. 7B is a side view of the lead engagement device of FIG. 7A.

Referring now to FIGS. 7A and 7B, another exemplary embodiment of a lead engagement device 700 according to the present disclosure is illustrated. The lead engagement device 700 generally includes a distal lead engagement portion 702 and a proximal handle portion (not shown), which may be the same or similar to the distal lead engagement portion 102 and a proximal handle portion 104 described above, respectively, except that the hypotube 704 further includes a plurality of tractability-enhancing features that facilitate maneuvering the lead engagement device 700 in tortuous anatomy. In some embodiments and as illustrated, such features may be a plurality of slits 706 that extend through the wall 708 from the inner surface 710 to the outer surface. In some embodiments and as illustrated, the slits 706 may be longitudinally offset from the fingers. In some embodiments and as illustrated, the slits 706 may be grouped at different longitudinal positions. In some embodiments and as illustrated, the slits 706 in each group may be circumferentially offset from the slits 706 in adjacent longitudinal groups.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A lead engagement device comprising:

a hypotube;

a plurality of lead engagement fingers comprising a plurality of segments of the hypotube, wherein the plurality of lead engagement fingers extends outwardly and in a first direction; and a plurality of apertures extending through a wall of the hypotube, wherein the plurality of apertures is formed from deformation of the plurality of lead engagement fingers, wherein the lead engagement device is configured to be positioned in a lead lumen of an implanted lead for removal of the implanted lead from a patient, wherein the plurality of lead engagement fingers is configured to engage the implanted lead and inhibit relative motion between the lead engagement device and the implanted lead when applying a first force to the lead engagement device in the first direction that the plurality of lead engagement fingers extend.

2. The lead engagement device of claim 1, wherein an inner lumen defines a longitudinal axis of the hypotube, wherein the plurality of apertures disposed in the wall of the hypotube are disposed in planes substantially parallel to the longitudinal axis of the hypotube, and wherein the plurality of lead engagement fingers are normally disposed at acute angles relative to the longitudinal axis.

3. The lead engagement device of claim 2, wherein a plane in which at least one of the acute angles is disposed falls within 0.0 to 0.1 inches of the longitudinal axis of the hypotube.

4. The lead engagement device of claim 2, wherein at least one of the acute angles is normally in a range of 5 to 45 degrees.

5. The lead engagement device of claim 1, wherein an inner lumen defines a longitudinal axis of the hypotube and circumferential direction extending about the longitudinal axis, wherein the plurality of fingers is curved in the circumferential direction.

6. The lead engagement device of claim 1, wherein at least one of the plurality of lead engagement fingers has a distal end coupled to the wall of the hypotube, a proximal free end opposite the distal end, and length between the distal end and the proximal free end in a range of 0.01 to 0.25 inches.

7. The lead engagement device of claim 6, wherein the plurality of lead engagement fingers is cantilevered from the wall.

8. The lead engagement device of claim 6, wherein the plurality of lead engagement fingers is monolithically coupled to the wall.

9. The lead engagement device of claim 1, wherein the plurality of lead engagement fingers has a first shape, and the plurality of apertures disposed in the wall of the hypotube have a second shape, the second shape being a same shape as the first shape.

10. The lead engagement device of claim 1, wherein the first shape and the second shape are rectangles.

11. The lead engagement device of claim 1, further comprising an outer sheath comprising an outer lumen, the outer lumen removably receiving the hypotube.

12. The lead engagement device of claim 1, wherein:

the wall comprises an inner surface defining an inner lumen and an outer surface opposite the inner surface; and the plurality of apertures extends through the wall between the inner surface and the outer surface.

13. The lead engagement device of claim 1, wherein the plurality of lead engagement fingers is configured to directly engage the lead lumen of the implanted lead.

14. The lead engagement device of claim 1, wherein the plurality of lead engagement fingers is configured to engage the implanted lead such that the plurality of segments of the hypotube directly contact the implanted lead.

15. The lead engagement device of claim 1, wherein the plurality of lead engagement fingers is configured to translate relative to the implanted lead and permit relative motion between the lead engagement device and the implanted lead when applying a second force to the lead engagement device in a second direction that is opposite to the first direction that the plurality of lead engagement fingers extend.

* * * * *